US008466198B2

(12) United States Patent
Kneller

(10) Patent No.: US 8,466,198 B2
(45) Date of Patent: Jun. 18, 2013

(54) COMPOSITIONS COMPRISING CREATINE SALTS AND METHODS OF USE THEREOF

(76) Inventor: Bruce Kneller, Randolph, MA (US)

( * ) Notice: Subject to any disclaimer, the term of this patent is extended or adjusted under 35 U.S.C. 154(b) by 205 days.

(21) Appl. No.: 12/202,944

(22) Filed: Sep. 2, 2008

(65) Prior Publication Data

US 2008/0319076 A1 Dec. 25, 2008

(51) Int. Cl.
*A61K 31/95* (2006.01)
*C07C 229/02* (2006.01)
*A61P 21/00* (2006.01)

(52) U.S. Cl.
USPC .......................................... 514/564; 562/560

(58) Field of Classification Search
USPC .......................................... 514/564; 562/560
See application file for complete search history.

(56) References Cited

U.S. PATENT DOCUMENTS

| | | | |
|---|---|---|---|
| 5,973,199 A | 10/1999 | Negrisoli et al. | |
| 6,114,379 A | 9/2000 | Wheelwright et al. | |
| 6,172,111 B1 | 1/2001 | Pischel et al. | |
| 6,211,407 B1 | 4/2001 | Thompson | |
| 6,399,611 B1 | 6/2002 | Golini | |
| 6,838,565 B2 | 1/2005 | Abraham et al. | |
| 7,329,763 B1 | 2/2008 | Molino | |
| 2002/0131987 A1* | 9/2002 | Carnazzo | 424/406 |
| 2005/0008678 A1* | 1/2005 | Howard et al. | 424/439 |

OTHER PUBLICATIONS

Maughan (Nutritional ergogenic aids and exercise performance, Nutrition Research Review (1999), 12, 255-280).*
Berge (Journal of Pharmaceutical Sciences, Jan. 1977, vol. 66, No. 1).*
Bal'Magiia, T.A., et al., Biull Eksp Biol Med. 79(3):18-21(1975).
Burke, D.G., et al., "Effect of creatine and weight training on muscle creatine and performance in vegetarians", Medicine & Science in Sports and Exercise. 35:1946-55(2003).
Dourodudos, I., et al., "Dose-related effects of prolonged NAHCO3 ingestion during high-intensity exercise", Medicine & Science in Sports & Exercise. 38(10):1746-53(2006).
Drago, F., et al. "Pyroglutamic acid improves learning and memory capacities in old rats", Functional Neurology. 3(2):137-43(1988).
Edge, J., et al., "Effects of chronic NaHCO₃ ingestion during interval training on changes to muscle buffer capacity, metabolism, and short term endurance performance", Journal of Applied Physiology. 101(3):918-25(2006).
Forbes, S., et al., "NaHCO3-induced alkalosis reduces the phisphocreatine slow component during heavy-intensity forearm exercise", Journal of Applied Physiology. 99(5):1668-75(2005).
Green, A.L., et al., "Carbohydrate ingestion augments skeletal muscle creatine accumulation during creatine supplementation in man", American Journal of Physiology. 271:E821-6(1996).
Greenhalf, P., et al., "Influence of oral creatine supplementation of muscle torque during repeated bouts of maximal voluntary exercise in man", Clinical Science. 85(5):565-571(1993).
Greenhalf, P., et al., "Effect of oral creatine supplementation on skeletal muscle phosphocreatine resynthesis", American Journal of Physiology. 266:E725-730(1994).
Grioli, S., et al., "Pyroglutamic acid improves the age associated memory impairment", Fundamental Clinical Pharmacology. 4: 169-73(1990).
Hultman. E., et al. "Muscle creatine loading in man", Journal of Applied Physiology. 81-232-37(1996).
Jowko, E., et al., "Creatine and beta-hydroxy-beta-methylbutyrate (HMB) additively increase lean body mass and muscle strength during a weight-training program", Nutrition. 17(7-8)558-566(2001).
Kirksey, K.B., et al., "The effects of 6 weeks of creatine monohydrate supplementation on performance measures and body composition in collegiate track and field athletes", Journal of Strength and Conditioning Research. 13:148-156(1999).
Kreider, R.B., et al., "Effects of creatine supplementation on body composition, strength and spring performance", Medicine and Science in Sports & Exercise. 30:73-82(1998).
Kreider, R.B., et al., "Effects of creatine supplementation on performance and training adaptations", Molecular and Cellular Biochemistry. 44: 89-94(2003).
MacJejewski, H., et al., Blood Lactate and Heat Stress during Training in Rowers. International Journal of Sports Medicine 28(11):945-951(2007).
McNaughton, Lars, "Sodium Bicarbonate ingestion and its effects on anaerobic exercise during various durations", Journal of Sports Sciences. 10(5):425-35(1992).
McNaughton, Lars, "Acute versus chronic sodium bicarbonate ingestion and anaerobic work and power output", Journal of Sports Medicine and Physical Fitness. 41(4):456-62(2001).
Mero, A., et al., "Combined creatine and sodium bicarbonate supplementation enhances interval swimming", Journal of Strength & Conditioning Research. 18(2):306-310(2004).
Mujika, I., et al., "Creatine supplementation and sprint performance in soccer players", Medicine & Science in Sports & Exercise. 32:518-525(2002).
Noonan, D., et al., "Effects of varying dosages of oral creatine relative to fat free body mass on strength and body composition", Journal of Strength and Conditioning Research. 12:104-108(1998).
Smekal, G., et al., "Respiratory Gas Exchange and Lactate Measures during Competitive Orienteering", Medicine & Science in Sports & Exercise. 35(4)682-689(2003).
Steenge, G.R., et al., "Protein- and carbohydrate-induced augmentation of whole body creatine retention in humans", Journal of Applied Physiology. 89:1165-1171(2000).
Stephens, T., et al., "Effect of sodium bicarbonate on muscle metabolism during intense endurance cycling", Medicine & Science in Sports & Exercise. 34:614-621(2002).

(Continued)

*Primary Examiner* — San-Ming Hui
*Assistant Examiner* — Kathrien Cruz
(74) *Attorney, Agent, or Firm* — Morse, Barnes-Brown & Pendleton, P.C.; Lisa M. Treannie, Esq.

(57) ABSTRACT

The invention relates to compositions (e.g., nutritional supplements) comprising, consisting essentially of, or consisting of a creatine bicarbonate, and to methods of making and using said compositions.

27 Claims, 1 Drawing Sheet

OTHER PUBLICATIONS

Stone, M.H., et al., "Effects of in-season (5 weeks) creatine and pyruvate supplementation on anaerobic performance and body composition in American football players", International Journal of Sports Nutrition. 9(2):146-165(1999).

Volek, J., et al., "Performance and muscle fiber adaptations to creatine supplementation and heavy resistance training", Medicine & Science in Sports & Exercise. 31:1147-1156(1999).

Williams, M. et al., "Creatine—The Power Supplement", Human Kinetics Publishers. 1-252 (1999).

Williams, M.H., et al., "Creatine supplementation and exercise performance: an update", Journal of the American College of Nutrition. 17:216-234(1998).

Willoughby, D.S., et al., "Effects of oral creatine and resistance training on myogenic regulatory factor expression", Medicine & Science in Sports and Exercise. 35:923-929(2003).

Willoughby, D.S., et al., "Effects of oral creatine and resistance training on myosin heavy chain expression", Medicine & Science in Sports and Exercise. 33:1674-81(2001).

Wiroth, J.B., et al., "Effects of oral creatine supplementation on maximal pedaling performance in older adults", European Journal of Applied Physiology. 84(6):533-539(2001).

* cited by examiner

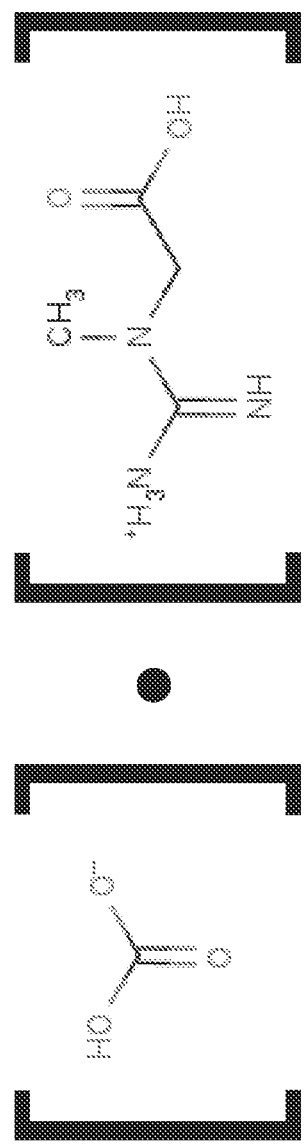

COMPOSITIONS COMPRISING CREATINE SALTS AND METHODS OF USE THEREOF

BACKGROUND OF THE INVENTION

Nutritional supplements and approaches for enhancing an athlete's muscle performance and the like (e.g., reducing fatigue, increasing strength, increasing endurance, etc.) have become popular exigencies in various sports and bodybuilding regimes. However, as athletes continually strive for improved muscle performance, there is a continuing need for new, more effective technologies to aid in increasing performance.

SUMMARY OF THE INVENTION

The invention relates to a nutritional supplement or nutraceutical, e.g., a food supplement, a food composition, comprising, consisting essentially of or consisting of a creatine salt, and to methods of making and using said creatine salt. In one embodiment of the invention the creatine salt is a creatine bicarbonate, i.e., a stable hydrosoluble salt consisting of (1) a creatine or creatine-like cation and (2) a bicarbonate anion. The creatine bicarbonate of the invention is superior to existing ionic salts of creatine due to its resistance to conversion to creatinine in aqueous solutions, its increased solubility, increased oral bioavailability, and ability to produce increased athletic function. Moreover the creatine bicarbonate of the invention is superior to existing bicarbonate salts due to the absence of sodium, magnesium, calcium and/or potassium, resulting in a composition which delivers less than the recommended daily allowance of these cations (e.g., none) to an individual to whom the composition is administered. In addition, the creatine bicarbonate composition has a self-buffering capability. The composition of the invention can be administered as a component of a nutritional supplement; the nutritional supplement may optionally contain small amounts of sodium (and/or calcium, magnesium and/or potassium) bicarbonate.

In one embodiment the invention relates to a composition comprising a creatine bicarbonate, wherein said creatine bicarbonate consists of a creatine or creatine-like cation and a bicarbonate anion. In embodiments in which the cation is a creatine-like cation, the creatine bicarbonate can be, for example, creatine ethyl ester bicarbonate, creatinol-O-bicarbonate, guanido propionic acid bicarbonate or guanido acetic acid bicarbonate. In preferred embodiments, the composition has increased solubility in organic mediums and aqueous solutions as compared to creatine; is more resistant to conversion to creatinine in organic mediums and aqueous solutions as compared to creatine; has increased tissue bioavailability in animals as compared to creatine; and/or has increased absorbability as compared to creatine. The composition can have one or more (combinations and subcombinations) improved functional properties.

In other embodiments the composition increases the skeletal muscle level of creatine in an animal; increases the skeletal muscle level of phosphocreatine in an animal; increases the skeletal muscle level of ATP in an animal; increases athletic performance in an animal; buffers plasma H+ levels in an animal during, before, and/or after exercise; increases plasma lactate level in an animal; and/or helps to induce a state of metabolic alkalosis in an animal. The composition can have one or more (combinations or subcombinations) of the listed physiological effects.

In preferred embodiments, the composition is a nutritional supplement comprising a creatine bicarbonate in an amount of from about 0.100 g to about 30.00 g, inclusive. In other embodiments the composition is a nutritional supplement comprising a creatine bicarbonate in an amount of from about 5% to about 100%, inclusive. In certain embodiments, the composition comprises additional active ingredients and/or is formulated for oral use.

The invention also relates to a method of increasing athletic performance in an animal comprising administering to the animal a composition comprising a creatine bicarbonate. In certain embodiments, the composition is a nutritional supplement comprising a creatine bicarbonate in an amount of from about 0.100 g to about 30.00 g, inclusive. In other embodiments, the composition is a nutritional supplement comprising a creatine bicarbonate in an amount of from about 5% to about 100%, inclusive.

In some embodiments, the administered composition increases the skeletal muscle level of creatine in said animal; increases the skeletal muscle level of phosphocreatine in said animal; increases the skeletal muscle level of ATP in said animal; buffers plasma H+ levels in said animal during, before, and/or after exercise; increases plasma lactate level in said animal; and/or helps to induce a state of metabolic alkalosis in said animal.

In other embodiments, the administered composition comprises other active ingredients and/or is administered orally.

The invention further relates to methods of making a creatine bicarbonate as described herein. In one embodiment the invention relates to a method of making a creatine bicarbonate comprising the steps of combining a source of bicarbonate anion and a source of creatine or creatine-like anion under conditions (e.g., time, temperature, vessel, phase) appropriate for molecular interaction of the cation and anion; separating (e.g., by filtering) the solid reaction product from residual liquid and collecting said solid reaction product, wherein said solid reaction product is a creatine bicarbonate; optionally resuspending said creatine bicarbonate in an appropriate liquid, separating said solid reaction product from residual liquid and collecting said solid reaction product, wherein said solid reaction product is creatine bicarbonate; and optionally reducing the particle size of said creatine bicarbonate. In particular embodiments the source of bicarbonate anion is hydrogen bicarbonate. In particular embodiments the source of creatine cation is creatine monohydrate.

BRIEF DESCRIPTION OF THE DRAWING

The FIGURE shows the chemical structure of (2-(1-methylguanido)acetyl)oxonium bicarbonate, a creatine bicarbonate, having a chemical formula of $C_5H_{11}N_3O_5$ and a molecular weight of about 192.15.

DETAILED DESCRIPTION OF THE INVENTION

Sodium bicarbonate (molecular weight of about 84.007, chemical formula=$NaHCO_3$) is an ionic salt consisting of a sodium (Na+) cation and a bicarbonate ($HCO_3-$) anion. The oral ingestion of sodium bicarbonate is known to improve athletic performance by increasing intracellular and extracellular $H^+$ ion buffering capacity via induction of metabolic alkalosis. Particular improvements in various parameters of athletic performance are discussed at length in the literature (e.g., *J Appl Physiol.* 101(3):918-25 (September 2006); *J Sports Sci.* 10(5):425-35 (October 1992); *J Sports Med Phys Fitness* 41(4):456-62 (December 2001); *Med Sci Sports Exerc* 38(10):1746-53 (October 2006); *Int J Sports Med. Nov.* 14 2007; *J Appl Physiol.* 99(5):1668-75 (November 2005)).

Oral administration of bicarbonate in the form of sodium bicarbonate improves athletic performance in trained and untrained members of both sexes in a variety of athletic settings. The increase in performance produced by the oral ingestion of $NaHCO_3$ is scalar and is directly related to the quantity of $NaHCO_3$ ingested.

However, there exist significant safety issues related to use of $NaHCO_3$. Typically, the effective oral dosage utilized is about 0.3 grams of $NaHCO_3$ per kilogram of body mass. Thus, a human with a body mass of 70 kilograms would need to ingest about 21 grams of $NaHCO_3$ to see a beneficial effect. As about 27.3% of the molecular weight of $NaHCO_3$ consists of sodium (Na+), ingesting 21 grams of $NaHCO_3$ would result in the ingestion of about 5.47 grams of sodium. The United States Recommended Daily Allowance (RDA) of sodium in a healthy, adult male is 2,400 mg (2.40 grams), while the National Academy of Sciences' Institute of Medicine suggests a daily allowance of sodium as low as 1,500 mg (1.50 grams). Thus, the ingestion of 0.3 grams of $NaHCO_3$ per kilogram of body mass in a 70 kg human would result in the ingestion of 2.23 to 3.64 times the suggested total daily dose of sodium.

Excessive sodium consumption can lead to a physiological condition called hypernatremia, a serious and potentially life-threatening condition. Symptoms of hypernatremia include nausea, vomiting, hypertension, dizziness, renal stress, heart failure, and, if untreated, coma and death. Additionally, it is well known to those in the art that a high plasma sodium level in humans is associated with muscle weakness, fatigue, and an overall decrease in performance. Thus, it is clear that improved agents are needed for delivery of bicarbonate in amounts sufficient to improve athletic performance without providing undesirable amounts of sodium to the recipient.

Creatine (molecular weight of about 131.134) is chemically known as a non-protein nitrogen, a compound which contains nitrogen but is not a protein per se. It is synthesized in the liver and pancreas from the amino acids arginine, glycine, and methionine. The average human has the capacity to store up to 160 grams of creatine under certain conditions (*J Nutrit Biochem.* 11:610-618 (1997)). The body breaks down about 1-2% of the creatine pool per day (about 1-2 grams per day) into creatinine, which is then excreted in the urine. Creatine stores can be replenished by obtaining creatine in the diet or through endogenous synthesis.

Creatine ingestion has been demonstrated to increase athletic performance; the average gain in athletic performance seen typically ranges from 10 to 15%, depending on the measured variable. For example, short term creatine monohydrate supplementation has been reported to improve maximal power/strength (5-15%), work performed during exercised of maximal effort muscle contractions (5-15%), single effort sprint performance (1-5%), and work performed during repetitive sprint performance (5-15%) (*Mol Cell Biochem* 244:89-94 (2003)). Nearly all studies indicate that proper creatine monohydrate supplementation increases body mass by about 1-2 kilograms in the first week of loading.

Current creatine oral supplementation typically relies on an ionic salt of creatine (e.g., creatine monohydrate, creatine pyruvate) in a powder form, which is dissolved in water and then taken orally. A variety of ionic salts of creatine are readily available as dietary supplements and are regulated by the U.S. Food & Drug Administration (FDA) under the Dietary Supplement Health and Education Act. However all of the ionic salts of creatine commercially available at present suffer from stability issues relating to their administration. The main problem with all existing creatine supplementation in this regard is the ability to deliver creatine in a form usable by the human body. It is well known in the art that existing ionic salts of creatine actually result in the ingestion by the human body of creatinine, which is a poisonous and toxic byproduct of creatine (creatine undergoes cyclization to creatinine, a process that is not reversible). It is believed that the main cause of complaints resulting from creatine consumption, namely stomach cramps, edema and dehydration, is the body's reaction to creatinine.

All commercially available ionic salts of creatine are dissolved in acidic solutions having a pH of from 3-6. It is known that at such pH levels, the conversion of creatine to creatinine is virtually instantaneous. Thus, a need exists for a nutritional supplement able to deliver usable creatine to mammals without substantial creatinine formation.

In view of the foregoing, it will be appreciated that the administration (e.g., oral administration) of a single composition incorporating both creatine and bicarbonate as a palatable ionic salt which retains, or even enhances, the bioeffectiveness of each would be a significant advancement in the art. As described herein, creatine bicarbonate provides a simultaneous action due to the use of creatine or creatine-like cations bonded to bicarbonate anions, which in turn provide improved athletic performance while acting as an efficient water soluble carrier or transporter that resists conversion to creatinine in solutions with an acidic pH. Accordingly, the invention relates to compositions (e.g., nutritional supplement, food supplement, dietary supplement) comprising, consisting essentially of, or consisting of a creatine bicarbonate, and to methods of making and using said compositions. As used herein, a nutritional supplement, also known as food supplement or dietary supplement, is a preparation for supplying effective agents that are missing or are not consumed in sufficient quantity in an individual's diet to have a desired effect. Typically the nutritional supplement is orally ingested, but it may also be administered via other routes.

Creatine bicarbonate (see, e.g., the FIGURE) is a white to off-white, crystalline solid compound that is hygroscopic and 2-25× more soluble in water that creatine monohydrate. Ingestion of a creatine bicarbonate promotes strength, endurance, recovery, and lean tissue and decreases fat tissue due to the creatine or creatine-like cation content, and provides a beneficial, physiological H+ buffering effect and induces metabolic alkalosis due to the bicarbonate anion content. The bicarbonate anion content also reduces phosphocreatine loss during intense exercise, thereby further decreasing the need for exogenous ingestion of creatine. A creatine bicarbonate may be administered to subjects (e.g., humans) with or without a high protein diet (about 1.25 to 2.0 grams protein/kilogram of body mass) and proper anaerobic training program in order to increase the variables associated with athletic function for the purpose of enhancing athletic performance. The oral, daily dose of a creatine bicarbonate can be from about 0.100 grams to about 30.00 grams per day; the preferred daily dosing schedule is a single dose of about 7.50-10.00 grams per day administered 30-90 minutes before workout in order to achieve optimal absorption and adequate muscle cell concentration. As used herein, the term "about" refers to a +/−10% variation from the nominal value. It is to be understood that such a variation is always included in any given value provided herein, whether or not it is specifically referred to.

A creatine bicarbonate can be made by any suitable method. Exemplary (non-limiting) embodiments of methods of making a creatine bicarbonate are described in the examples.

In some embodiments of the invention the composition (i.e., a creatine bicarbonate or a nutritional supplement comprising a creatine bicarbonate) is formulated as a tablet, capsule, caplet, powder, suspension, gel preparation, aqueous solution, solid food form (e.g., chewable bar or wafer), or liquid dosage form such as elixirs, syrups, dispersed powders, granules or emulsions. In one embodiment the composition is particularly formulated for oral use.

In addition, the creatine bicarbonate can be administered before, concurrent with or after other optional components such as other active ingredients. In some embodiments the nutritional supplement composition comprising a creatine bicarbonate contains one or more of the following ingredients, preferably as an active ingredient:

Carbohydrates including, but not limited to, isomaltulose, trehalose, maltodextrin, glucose, sucrose, fructose, lactose, amylose, and/or ribose;

Water soluble vitamins including, but not limited to, Vitamin C, Vitamin B1, Vitamin B2, Vitamin B3, Vitamin B6, Vitamin B12, and/or Vitamin K (and derivatives);

Minerals including, but not limited to, calcium, sodium, potassium, chromium, vanadium, magnesium, and/or iron (and derivatives)(preferably in amounts less than the RDA);

Amino acids including, but not limited to, L-arginine, L-ornithine, L-glutamine, L-tyrosine, L-taurine, L-leucine, L-isoleucine, and/or L-valine (and derivatives);

Nutraceutically acceptable stimulants including, but not limited to, methylxanthines (e.g.—caffeine) and/or glucuronolactone (and derivatives);

Nutraceutically acceptable hypoglycemic agents including, but not limited to, alpha-lipoic acid and its derivatives, cinnamon bark, bitter melon extracts, Gymnema Sylvestre extracts, 4-hydroxy-isoleucine, corosolic acid, and/or D-pinitol (and derivatives);

Creatine and its salts (e.g., creatine monohydrate), esters (e.g., creatine ethyl ester), chelates, amides, ethers (and derivatives);

Adenosine triphosphates and its disodium salt;

Glycerol and glycerol monostearate;

Mannitol;

Sorbitol; and

Dextran.

Preferably the composition comprises from about 5% to about 100% creatine bicarbonate, more preferably about 20% to about 100% creatine bicarbonate, and even more preferably about 50% to about 100% creatine bicarbonate.

As used herein, the terms "nutraceutical" and nutraceutically acceptable" are used herein to refer to any substance that is a food or part of a food and provides medical or health benefits, including the prevention and treatment of disease. Hence, compositions falling under the label "nutraceutical" or "nutraceutically acceptable" may range from isolated nutrients, nutritional or dietary supplements, and specific diets to genetically engineered designer foods, herbal products, and processed foods such as cereals, soups, and beverages. In a more technical sense, the term has been used to refer to a product isolated or purified from foods, and generally sold in medicinal forms not usually associated with foods and demonstrated to have a physiological benefit or provide protection against chronic disease.

As used herein, the term "derivative" can include salts, esters, ethers, amides, chelates, lactone forms, hydrates, or complexes of stated chemicals. Such derivatives can also include stereoisomers or structural isomers, so long as the derivative operates similarly and produces the desired effect. Alternatively, the derivative can be a precursor to the stated chemical, which subsequently undergoes a reaction in vivo to yield the stated chemical or derivative thereof. By way of non-limiting example only, ubiquinol is a useful derivative of ubiquinone, and acetyl-L-carnitine, carnitine hydrochloride, and the D and L stereoisomers of carnitine are useful derivatives of L-carnitine.

The compositions may contain pharmaceutically, e.g., nutraceutically, acceptable excipients, according to methods and procedures well known in the art. As used herein, "excipient" refers to substances that are typically of little or no therapeutic value, but are useful in the manufacture and compounding of various pharmaceutical preparations and which generally form the medium of the composition. These substances include, but are not limited to, coloring, flavoring, and diluting agents; emulsifying, dispersing and suspending agents, ointments, bases, pharmaceutical solvents; antioxidants and preservatives; and miscellaneous agents. Suitable excipients are described, for example, in Remington's Pharmaceutical Sciences, which is incorporated herein by reference in its entirety.

The nutritional supplement compositions according to the present invention can further comprise one or more acceptable carriers. A wide number of acceptable carriers are known in the nutritional supplement arts, and the carrier can be any suitable carrier. The carrier need only be suitable for administration to animals, including humans, and be able to act as a carrier without substantially affecting the desired activity of the composition. Also, the carrier(s) may be selected based upon the desired administration route and dosage form of the composition. For example, the nutritional supplement compositions according to the present invention are suitable for use in a variety of dosage forms, such as liquid form and solid form (e.g., a chewable bar or wafer). In desirable embodiments, as discussed below, the nutritional supplement compositions comprise a solid dosage form, such as a tablet or capsule. Examples of suitable carriers for use in tablet and capsule compositions include, but are not limited to, organic and inorganic inert carrier materials such as gelatin, starch, magnesium stearate, talc, gums, silicon dioxide, stearic acid, cellulose, and the like. Desirably, the carrier is substantially inert, but it should be noted that the nutritional supplement compositions of the present invention may contain further active ingredients in addition to creatine bicarbonate.

Methods of Use

The compositions and methods of the present invention may provide significant increase or improvement in athletic performance, e.g., muscle size, and/or muscle strength, and/or muscle endurance in individuals. As used herein, "athletic performance" and/or "athletic functions" refers to the sum of physical attributes which can be dependent to any degree on skeletal muscle contraction. For example, athletic performance and/or athletic functions include, but are not limited to, maximal muscle power, muscular endurance, running speed and endurance, swimming speed and endurance, throwing power, lifting and pulling power.

While it is expected that the compositions and methods of the present invention will be of particular importance to bodybuilders and other athletes, the usefulness of compositions and methods of the invention is not limited to those groups. Rather, any individual may beneficially use the compositions and methods of the invention. Indeed, the disclosed compositions and methods have application to all animals, including mammals, birds and reptiles. As used herein, the term "animal" includes all members of the animal kingdom, preferably mammals (e.g., dogs, horses, cows, mules), more preferably humans. For example, the nutritional supplements of the invention may have beneficial effect for competitive animals (e.g., racehorses, show horses, racing dogs (e.g., greyhounds), bird dogs, show dogs) and work animals (e.g., horses, mules and the like) in whom an increase in muscle performance is desirable.

The compositions according to the present invention may be employed in methods for supplementing the diet of an individual, e.g., an athlete, and/or for enhancing an individual's muscle mass and/or muscle size and/or strength, and/or endurance. Accordingly, the present invention provides methods of supplementing the dietary intake of an individual comprising administering to the individual an effective amount of a composition (e.g., a creatine bicarbonate or a nutritional supplement comprising a creatine bicarbonate) according to the present invention to increase athletic performance or athletic function is said individual. The invention also relates to methods of improving athletic performance and/or athletic function in an individual comprising administering an effective amount of a creatine bicarbonate (alone or in combination with other agents, e.g., in a nutritional supplement) to the individual.

As used herein, an "effective amount" of compositions of the present invention is defined as an amount effective, at dosages and for periods of time necessary, to achieve the desired result. The effective amount of compositions of the invention may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present invention may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

The embodiments set forth in the present application are provided only to illustrate various aspects of the invention and additional embodiments and advantages of the food supplements and methods of the present invention will be apparent to those skilled in the art. The teachings of all references cited herein are incorporated herein by reference in their entirety.

EXAMPLES

Methods of Making a Creatine Bicarbonate

Example 1

Step 1 6.1059 grams (0.10 moles) of hydrogen carbonate (RN:71-52-3, 99% purity) are added to 100 milliliters of ethyl acetate in a beaker. A stir bar is placed inside, and the mixture is stirred for 10-15 minutes.
Step 2 14.913 grams (0.10 moles) of creatine monohydrate are then added to the stirred suspension from Step 1 at 20-25° C., and this mixture is allowed to stir for about 3 hours at 25° C.
Step 3 A white, finely crystalline product can be obtained and separated out by filtering the mixture from Step 2. The filtrate is discarded, and a crystalline residue can be collected.
Step 4 The crystalline residue from Step 3 is then suspended in 100 milliliters of 99% pure ethyl acetate and then filtered again. This step is repeated 2-3 times.
Step 5 The "washed" material from Step 4 is placed into a beaker and the remaining solvent is allowed to evaporate overnight. About 10.55 grams of creatine bicarbonate is recovered for a yield of >50%.

Example 2

Step 1 6.1059 grams (0.10 moles) of hydrogen bicarbonate (RN: 71-52-3, 99% purity) are added to 20 milliliters of distilled, deionized water in a beaker. The mixture is heated to 30° C. and stirred mechanically for 15-20 minutes.
Step 2 14.913 grams (0.10 moles) of creatine monohydrate are added to the mixture from Step 1, and allowed to stir for 30-40 minutes until concentrated (i.e., a slurry-like consistency) and then cooled to 5° C.
Step 3 The mixture from Step 2 is filtered, and the solid residue is collected.
Step 4 The collected product from Step 3 is suspended in 50 milliliters of anhydrous ethanol to remove any residual water.
Step 5 The mixture from Step 4 is filtered, and the solid residue is recovered.
Step 6 The collected, solid crystalline residue from Step 5 is placed in a beaker, and the remaining solvent is allowed to evaporate overnight. About 8.63 grams of creatine bicarbonate is recovered for a yield of approximately 45%.

Example 3

Step 1 A reactor is charged with about 2.400 gallons of anhydrous methanol to which about 416.55 kilograms (about 6,845 moles) of hydrogen bicarbonate is then added at 20-30° C. Any commercially available, food grade hydrogen bicarbonate may be used. The mixture is stirred until all the hydrogen bicarbonate is dissolved.
Step 2 About 1,025 kilograms (about 6,845 moles) of creatine monohydrate is added to the mixture from Step 1 with continued mixing/agitation at approximately 20-30° C. Any commercially available, food grade creatine monohydrate may be used. Once all the creatine monohydrate is added, stirring at 20-30° C. continues for 4-6 hours to allow all the materials to react.
Step 3 The end product is creatine bicarbonate, which may be separated out via, e.g., crystallization, optionally preceded by distillation to concentrate the product. One skilled in the art will recognize other acceptable separation methods suitable for separating the creatine bicarbonate.
Step 4 The crystallized creatine bicarbonate from Step 3 is filtered from the reaction mixture and collected. This filtrate is washed with anhydrous methanol to remove any by products or other impurities. The resultant crystalline creatine bicarbonate product is dried at a suitable temperature, and the material may then be ground or milled to a desirable particle size and then packaged.

Methods of Use

The servings set forth in these examples are designed for athlete with a body mass of about 70 kilograms. Daily values can be increased or decreased depending on the body mass of the individual athlete.

Example 1

In this example, an athlete consumes four servings of a food supplement as described herein daily, that is, a serving of the food supplement about every six hours. Each serving of the food supplement is about 7.50 grams and contains 7.50 grams of creatine bicarbonate. Each 7.50 gram serving is administered as a powder dissolved into about 300-500 milliliters of water or fruit juice to provide a liquid drink.

Example 2

In this example, an athlete consumes one serving of the food supplement as described herein daily; typically the athlete will consume a serving of the food supplement about 30-90 minutes before exercise. Each serving is about 103.50 grams and contains the following:
Creatine bicarbonate 7.50 grams;
Maltodextrin 50.00 grams; and
Whey protein concentrate 46.00 grams.

Each approximate 103.50 gram serving is mixed in about 500-1000 milliliters of water or fruit juice to provide a liquid drink.

Example 3

In this example, an athlete consumes one serving of the food supplement described herein daily; typically the athlete will consume a serving of the food supplement about 60 minutes before exercise. Each serving is about 69.40 grams and contains the following:
Creatine bicarbonate 4.50 grams;
L-Leucine 4.00 grams;
L-Carnitine 5.00 grams;
Ubiquinone 0.100 grams;
L-Taurine 3.00 grams;
L-Glutamine 7.50 grams;
L-Tyrosine 2.00 grams;
Disodium ATP 0.200 grams;
Mannitol 5.00 grams;
Partially Hydrolyzed Guar Gum 5.00 grams;
Isomalulose 10.00 grams;
Ribose 5.00 grams;
Glucose 15.00 grams;
Calcium Phosphate 3.00 grams; and
4-hydroxyisoleucine 0.100 grams.

Each approximate 69.40 gram serving is mixed in about 500-750 milliliters of water or juice to provide a liquid drink.

What is claimed is:

1. A composition comprising a creatine bicarbonate, wherein said creatine bicarbonate is a hydrosoluble salt consisting of a creatine and a bicarbonate anion.

2. A composition according to claim 1 wherein the composition has increased solubility in organic mediums and aqueous solutions as compared to creatine.

3. A composition according to claim 1 wherein the composition is more resistant to conversion to creatinine in organic mediums and aqueous solutions as compared to creatine.

4. A composition according to claim 1 wherein the composition has increased tissue bioavailability in animals as compared to creatine.

5. A composition according to claim 1 wherein the composition has increased absorbability as compared to creatine.

6. A composition according to claim 1 wherein the composition increases the skeletal muscle level of creatine in an animal.

7. A composition according to claim 1 wherein the composition increases the skeletal muscle level of phosphocreatine in an animal.

8. A composition according to claim 1 wherein the composition increases the skeletal muscle level of ATP in an animal.

9. A composition according to claim 1 wherein the composition increases athletic performance in an animal.

10. A composition according to claim 1 wherein the composition buffers plasma H+levels in an animal during, before, and/or after exercise.

11. A composition according to claim 1 wherein the composition increases plasma lactate level in an animal.

12. A composition according to claim 1 wherein the composition helps to induce a state of metabolic alkalosis in an animal.

13. A composition according to claim 1 wherein the composition is a nutritional supplement comprising a creatine bicarbonate in an amount of from about 0.100 g to about 30.00 g, inclusive.

14. A composition according to claim 1 wherein the composition is a nutritional supplement comprising a creatine bicarbonate in an amount of from about 5% to about 100%, inclusive.

15. A composition according to claim 1 wherein the composition comprises additional active ingredients.

16. A composition according to claim 1 wherein the composition is formulated for oral use.

17. A method of increasing athletic performance in an animal comprising administering to the animal a composition comprising a creatine bicarbonate, wherein said creatine bicarbonate is a hydrosoluble salt consisting of a creatine and a bicarbonate anion.

18. A method according to claim 17 where the composition is a nutritional supplement comprising a creatine bicarbonate in an amount of from about 0.100 g to about 30.00 g, inclusive.

19. A method according to claim 17 wherein the composition is a nutritional supplement comprising a creatine bicarbonate in an amount of from about 5% to about 100%, inclusive.

20. A method according to claim 17 wherein the composition increases the skeletal muscle level of creatine in said animal.

21. A method according to claim 17 wherein the composition increases the skeletal muscle level of phosphocreatine in said animal.

22. A method according to claim 17 wherein the composition increases the skeletal muscle level of ATP in said animal.

23. A method according to claim 17 wherein the composition buffers plasma H+levels in said animal during, before, and/or after exercise.

24. A method according to claim 17 wherein the composition increases plasma lactate level in said animal.

25. A method according to claim 17 wherein the composition helps to induce a state of metabolic alkalosis in said animal.

26. A method according to claim 17 wherein the composition comprises other active ingredients.

27. A method according to claim 17 wherein the composition is administered orally.

* * * * *